(12) United States Patent
Sasaki et al.

(10) Patent No.: US 7,699,779 B2
(45) Date of Patent: Apr. 20, 2010

(54) ULTRASONIC TREATMENT EQUIPMENT

(75) Inventors: Kazuaki Sasaki, Kawasaki (JP);
Takashi Azuma, Kawasaki (JP);
Ken-ichi Kawabata, Kodaira (JP);
Shin-ichiro Umemura, Hachioji (JP);
Takashi Okai, Tokyo (JP); Tetsuya Ishikawa, Yokohama (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 713 days.

(21) Appl. No.: 10/557,237

(22) PCT Filed: May 18, 2004

(86) PCT No.: PCT/JP2004/007057

§ 371 (c)(1),
(2), (4) Date: Feb. 6, 2007

(87) PCT Pub. No.: WO2004/100811

PCT Pub. Date: Nov. 25, 2004

(65) Prior Publication Data
US 2007/0161897 A1    Jul. 12, 2007

(30) Foreign Application Priority Data
May 19, 2003    (JP)    ............................. 2003-139753

(51) Int. Cl.
*A61B 8/00*    (2006.01)
(52) U.S. Cl. ........................ 600/439; 600/437; 600/453; 600/454; 600/456
(58) Field of Classification Search ................. 600/407, 600/437
See application file for complete search history.

(56) References Cited

U.S. PATENT DOCUMENTS

| 4,905,672 | A |   | 3/1990 | Schwarze et al. |
| 5,769,790 | A | * | 6/1998 | Watkins et al. ............... 600/439 |
| 2002/0077549 | A1 | * | 6/2002 | Davidson et al. ............ 600/439 |

(Continued)

FOREIGN PATENT DOCUMENTS

JP    62-139645    6/1987

(Continued)

*Primary Examiner*—Long V Le
*Assistant Examiner*—Joel F Brutus
(74) *Attorney, Agent, or Firm*—Antonelli, Terry, Stout & Kraus, LLP.

(57) ABSTRACT

Ultrasonic treatment equipment is provided which repeats therapeutic ultrasound exposure while measuring a degree of vessel constriction on a therapeutic ultrasound exposure basis. This equipment includes: a therapeutic ultrasonic transducer 2 which exposes a blood vessel of an affected part to a focused therapeutic ultrasonic wave for a specified period of exposure time; an imaging ultrasonic probe 3 which images an ultrasound tomographic image of the affected part; a display unit 24 which displays the ultrasound tomographic image; means 21 for detecting a blood flow signal from a signal received by the imaging ultrasonic probe and determining the blood flow velocity of the blood vessels of the affected part; means 21 for calculating a rate of change in blood flow velocity during the exposure to the therapeutic ultrasonic wave or before and after the exposure to the therapeutic ultrasonic wave; and means 23 for controlling exposure conditions of the therapeutic ultrasonic wave on the basis of the rate of change in blood flow velocity, and thereby controlling the therapeutic ultrasonic transducer.

14 Claims, 9 Drawing Sheets

U.S. PATENT DOCUMENTS

2003/0018256 A1 1/2003 Sasaki et al.
2004/0153126 A1 8/2004 Okai

FOREIGN PATENT DOCUMENTS

| JP | 2002-224114 | 8/2002 |
| JP | 2003-079626 | 3/2003 |
| JP | 2004-154205 | 6/2004 |
| WO | WO 02/100486 | 12/2002 |

* cited by examiner

ULTRASONIC TREATMENT EQUIPMENT

FIELD OF THE INVENTION

The present invention relates to ultrasonic treatment equipment used for treating tumors.

BACKGROUND OF THE INVENTION

Ultrasonic waves have characteristics that electromagnetic waves such as a laser beam and a microwave never provide in that the former deeply propagates inside a living-body at short wavelengths and can be focused on an arbitrary point. Research and development of ultrasonic therapy which make good use of these characteristics have been actively advanced. The effects of ultrasonic waves on a living body, which can be made use of at the time of treatment, are roughly classified into thermal effects and sonochemical effects. The former thermal effects are produced when tissue absorbs an ultrasonic wave and consequently heat is generated. The treatments that medically use the thermal effects are roughly classified into "hyperthermia" and "heat coagulation therapy". Hyperthermia involves continuously heating an affected part to about 40 to 50° C. for treating tumors or the like. Heat coagulation therapy involves using high intensity focused ultrasound (HIFU) to heat a minute region of an affected part in a short period of time up to a temperature of, e.g., 70 to 100° C., which can cause tissue denaturation.

"Hyperthermia" used for treating tumors is a therapy that makes use of the characteristic that tumor cells are weak in persistent high temperature (about 43° C.) as compared with normal cells. Although slowing the growth of a tumor, however, hyperthermia does not reach the satisfactory level for treatment because of the following disadvantages: The capability of directly and drastically necrotizing tumor cells is low. Since the increase in temperature of an affected part is controlled by the blood flow of the tissue surrounding the affected part and heat conduction, it is not easy to keep temperature required for treatment unchanged. In addition, since a temperature-increasing region is not sufficiently localized, the balance between curative effects and stress (side effect) on a living body is not satisfactorily achieved. The hyperthermia, therefore, is often used as combined therapy in combination with radiation therapy in the actual clinical field.

On the other hand, heat coagulation therapy using HIFU involves focusing a high intensity ultrasonic wave on a minute region having a size of the order of millimeters so as to increase the temperature to a level at which tissue denaturation is immediately caused. The heat coagulation therapy using HIFU is different from hyperthermia described above in temperature increasing at a target region to be treated, and in a change in tissue caused by the increased temperature. Heat generated in tissue is carried away by heat conduction and the blood flow. In the case of heat coagulation therapy, however, a high intensity ultrasonic wave increases the temperature in a focused part to a temperature level of the protein coagulation or more to cause the coagulation in a period of time that is much shorter than a period of time (about 1 minute) required until the heat transport and the heat generation caused by the ultrasonic wave enter an equilibrium state. Since the ultrasonic wave density is low in regions other than a region corresponding to a focus, the temperature in these regions does not reach the temperature of heat denaturation. As a result, the tissue denaturation occurs only in a region close to the focus. At present, the therapy using HIFU is applied to therapy for prostatic hyperplasia, prostatic cancer, and uterine fibroid.

SUMMARY OF THE INVENTION

In the conventional heat coagulation therapy, a region in which focused ultrasonic wave exposure causes irreversible heat denaturation of the tissue is close to a focus, and the volume of the region is very small. The volume of a region that can be treated at a time is small. Therefore, when the entire tumor is to be treated, it is necessary to repeat the exposure while moving a focus moved.

Moreover, in a case of performing exposure a plurality of times, the next exposure must be performed after the temperature of the tissue other than a target to be treated, which has been increased by the last exposure, is sufficiently decreased by cooling effects of the blood flow, and the like. Accordingly, the wait time is required between exposure cycles.

Therefore, when a tumor having a size of several centimeters is treated, the treatment time may extend over several hours. Thus, the current heat coagulation therapy has a large problem of the increased treatment time. Under the existing circumstances, there is a problem in that, for example, the treatment efficiency in particular for a tumor with a large volume, such as uterine fibroid, is remarkably low. Further, when HIFU is aimed at a blood vessel for exposure, coagulation effects on the blood vessel are not kept constant. Accordingly, the coagulation effects are often uncertain. Under the existing circumstances, there is another problem in that it is not possible to judge effects on blood vessels on a HIFU basis.

Recently, as a method for treating uterine fibroid, liver cancer, and the like, the arterial embolization therapy is being tried. This treatment method involves inserting a catheter into a feeding vessel of the tumor and injecting an infarction material into the blood vessel. The injected infarction material blocks the feeding vessel that returns to the tumor, which interrupts the blood flow. As a result, furnishing of nutrition to the tumor is stopped, and thus the tumor is treated. In general, it is known that as a tumor such as uterine fibroid has a smaller amount of blood flow, tumor regression effects produced by the interruption of the blood flow become stronger. This treatment method, however, involves inserting a catheter from a main artery located at the base of the thigh or the like of a patient under general anesthesia or local anesthesia, and introducing the catheter up to a blood vessel of a target region under fluoroscopy. Accordingly, the patient is much exposed to X-radiation, and much suffers from the insertion of the catheter.

Here, another example of the method for treating such a tumor could conceivably be a treating method that involves directing a focused ultrasonic wave from the outside of the body to a blood vessel that supplies the tumor with nutrition, thereby causing the blood vessel to become infarcted, interrupting the supply of nutrition to the tumor noninvasively or minimally invasively. It is probable that this treatment method can achieve the purpose of treating tumors such as uterine fibroid having a curative effect through the above-stated blood flow interruption with exposure in a much shorter period of time as compared with the method of treating a tumor by directing a focused ultrasonic wave to the entire tumor. However, when HIFU is aimed at a target blood vessel to expose the blood vessel thereto, it is not easy to correctly coagulate the blood vessels with the HIFU being long and narrowly focused. Therefore, coagulation effects on the blood vessel are often uncertain. For example, if a position at which the HIFU is aimed slightly deviates from the target blood vessel, or a position of the target blood vessel goes out from a focus due to a change in motion of a patient body during the exposure, coagulation effects on the blood vessel may be insufficient. In addition, since blood vessels are different from each other in size, the number of times or intensities of HIFU exposure required for constriction and infarction are different from each other. Accordingly, what is desired is a technology for keeping track of a degree of constriction of blood vessels on a HIFU exposure basis and certainly causing vessel infarction.

An object of the present invention is to provide ultrasonic treatment equipment that is capable of repeating exposure to a therapeutic ultrasonic wave while measuring a degree of vessel constriction on a therapeutic ultrasound exposure basis.

In order to achieve the above-mentioned object, according to one aspect of the present invention, there is provided ultrasonic treatment equipment comprising: a therapeutic ultrasonic transducer which exposes a blood vessel of an affected part to a focused therapeutic ultrasonic wave for a specified period of exposure time; an imaging ultrasonic probe which images an ultrasound tomographic image of the affected part; a display unit which displays the ultrasound tomographic image; means for detecting a blood flow signal from a signal received by the imaging ultrasonic probe and determining the blood flow velocity of the blood vessel of the affected part; means for calculating a rate of change in blood flow velocity during the exposure to the therapeutic ultrasonic wave or before and after the exposure to the therapeutic ultrasonic wave; and means for controlling exposure conditions of the therapeutic ultrasonic wave on the basis of the rate of change in blood flow velocity, and thereby controlling the therapeutic ultrasonic transducer.

The ultrasonic treatment equipment according to the present invention measures the blood flow velocity of the blood vessel to which the therapeutic ultrasonic wave has been exposed, and then compares the blood flow velocity before the exposure to the therapeutic ultrasonic wave with that after the exposure to the therapeutic ultrasonic wave, thereby making it possible to evaluate a degree of constriction of the blood vessel or a degree of infarction of the blood vessel, and to recognize whether or not the blood vessel has been correctly exposed to the therapeutic ultrasonic wave.

To be more specific, as a result of aiming at a blood vessel region and exposing the blood vessel in the region to the therapeutic ultrasonic wave, if there is a substantial change in blood flow velocity that indicates predetermined constriction of the blood vessel, it can be judged that this ultrasound exposure is correctly aimed at the blood vessel and accordingly the ultrasound exposure is effective. Therefore, repeating the ultrasound exposure in the same region makes it possible to efficiently promote the constriction of the blood vessel in stages. To be more specific, by repeating the exposure while making a judgment as to whether or not the exposure has caused the vessel constriction on the basis of a change in blood flow velocity on an ultrasound exposure basis, it is possible to achieve the vessel infarction, and thereby to interrupt feeding vessels of the tumor.

On the other hand, as a result of aiming at a blood vessel region and exposing the blood vessel in the region to the therapeutic ultrasonic wave, if there is no substantial change in blood flow velocity indicating that the constriction of the blood vessel has occurred, it is shown that effects produced by this exposure are not sufficient for constricting the target blood vessel. In other words, this means that the therapeutic ultrasonic wave has not been correctly aimed at the blood vessels, or that a condition, such as the intensity of the therapeutic ultrasonic wave, the exposure time or the like is not optimally set. Therefore, it becomes possible to end the ultrasound exposure, or it also becomes possible to prompt an operator to set therapeutic protocols again. In another case, it is also possible to change the exposure conditions of the ultrasonic wave in like manner before the exposure is performed again.

According to the above configurations, it is possible to cause a target blood vessel to certainly become infarcted by repeating the exposure to a therapeutic ultrasonic wave while measuring a degree of vessel constriction on a therapeutic ultrasound exposure basis. To be more specific, the ultrasonic treatment equipment according to the present invention is capable of treating a tumor by exposing blood vessels for feeding the tumor to an ultrasonic wave to cause the blood vessels to be constricted or become infarcted, attenuating or blocking the blood flow thereof.

DESCRIPTION OF THE PREFERRED EMBODIMENT

Figure 1:
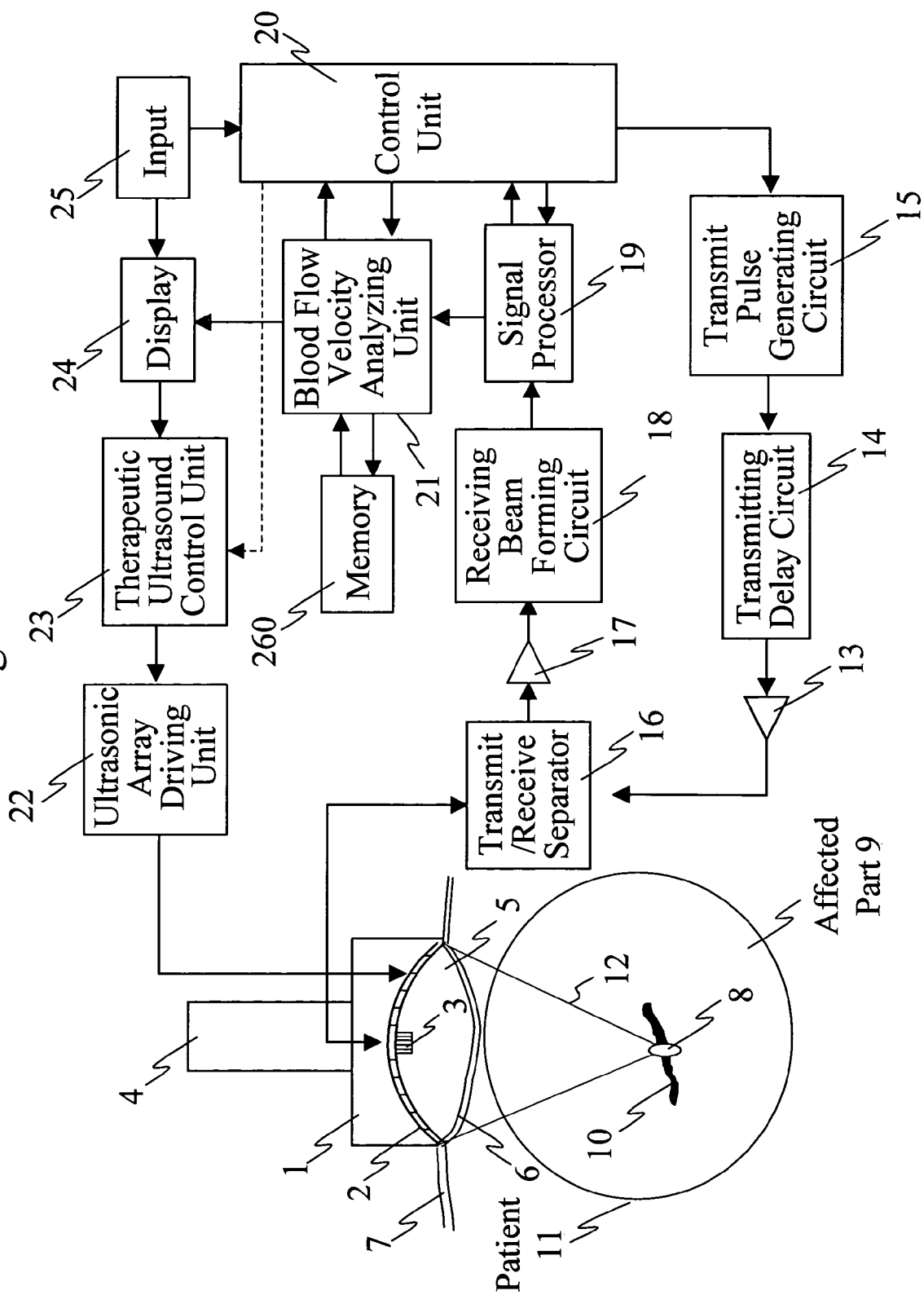
FIG. 1 is a diagram schematically illustrating the configuration of ultrasonic treatment equipment according to an embodiment of the present invention.

In ultrasonic treatment equipment according to the present invention, therapeutic ultrasound exposure is repeated a plurality of times while measuring a degree of vessel constriction on a therapeutic ultrasound exposure basis.

Ultrasonic treatment equipment according to a first configuration of the present invention comprises: a therapeutic ultrasonic transducer which exposes a blood vessel of an affected part to a focused therapeutic ultrasonic wave for a specified period of exposure time; an imaging ultrasonic probe which images an ultrasound tomographic image of the affected part; a display unit which displays the ultrasound tomographic image; means for comparing the blood flow velocity of the blood vessel before the exposure to the therapeutic ultrasonic wave with that after the exposure to the therapeutic ultrasonic wave, and thereby calculating a rate of change in blood flow velocity, wherein the therapeutic ultrasonic wave exposure causes the blood vessel of the affected part to be constricted or become infarcted.

The ultrasonic treatment equipment according to the first configuration of the present invention further comprises means for detecting a blood flow signal from a signal received by an imaging ultrasonic probe to determine the blood flow velocity of the blood vessel of the affected part, wherein if the rate of change in blood flow velocity before and after the therapeutic ultrasonic wave exposure is within a range of a predetermined rate of change, the therapeutic ultrasonic wave exposure is repeated, whereas if the rate of change in blood flow velocity before and after the therapeutic ultrasonic wave exposure is out of the range of the predetermined rate of change, the therapeutic ultrasonic wave exposure is ended.

The display unit displays any one of the following items:

(1) the ultrasound tomographic image of the affected part, the blood flow velocity before and after the therapeutic ultrasonic wave exposure, and the rate of change in blood flow velocity before and after the therapeutic ultrasonic wave exposure;

(2) the ultrasound tomographic image of the affected part, and a vessel constriction rate acquired on the basis of the rate of change in blood flow velocity before and after the therapeutic ultrasonic wave exposure;

(3) the ultrasound tomographic image of the affected part, and at least one of the number of repeat times, intensity, and specified time of period, of the therapeutic ultrasonic wave exposure; and (4) the ultrasound tomographic image of the affected part, a region subjected to the therapeutic ultrasonic wave, and exposure conditions of the therapeutic ultrasonic wave.

Moreover, the ultrasound tomographic image of the affected part is displayed in time series together with the exposure conditions of the therapeutic ultrasonic wave that has been applied a plurality of times.

Ultrasonic treatment equipment according to a second configuration of the present invention comprises: a therapeutic ultrasonic transducer which exposes a blood vessel of an affected part to a focused therapeutic ultrasonic wave for a specified period of exposure time; an imaging ultrasonic probe which images an ultrasound tomographic image of the affected part; a display unit which displays the ultrasound tomographic image; means for detecting a blood flow signal from a signal received by the imaging ultrasonic probe to determine the blood flow velocity of the blood vessel of the affected part; means for controlling the therapeutic ultrasonic wave exposure on the basis of a change in blood flow velocity before and after the therapeutic ultrasonic wave exposure, wherein the therapeutic ultrasonic wave exposure causes the blood vessel of the affected part to be constricted or become infarcted.

Moreover, in the ultrasonic treatment equipment according to the second configuration of the present invention, if the change in blood flow velocity is an increasing change, the therapeutic ultrasonic wave exposure is repeated, whereas if the change in blood flow velocity is a decreasing change, and the blood flow velocity after the therapeutic ultrasonic wave exposure is lower than or equal to a predetermined threshold value, the therapeutic ultrasonic wave exposure is ended.

The display unit displays any one of the following items:

(1) the ultrasound tomographic image of the affected part, the blood flow velocity before and after the therapeutic ultrasonic wave exposure, and the rate of change in blood flow velocity;

(2) the ultrasound tomographic image of the affected part, and a vessel constriction rate acquired on the basis of the rate of change in blood flow velocity before and after the therapeutic ultrasonic wave exposure; and (3) the ultrasound tomographic image of the affected part, a region subjected to the therapeutic ultrasonic wave, and exposure conditions of the therapeutic ultrasonic wave.

Moreover, the ultrasound tomographic image of the affected part is displayed in time series together with the exposure conditions of the therapeutic ultrasonic wave that has been applied a plurality of times.

Embodiments of ultrasonic treatment equipment according to the present invention will be described with reference to drawings below.

FIG. 1 is a diagram schematically illustrating a configuration of ultrasonic treatment equipment according to an embodiment of the present invention.

A therapeutic applicator 1 comprises: a therapeutic ultrasound transducer 2 constituted of one or more spherical therapeutic ultrasonic wave elements, each of which emits a high intensity therapeutic ultrasonic wave; a medium 5 for leading the high intensity ultrasonic wave to skin 7 of a patient 11; a water bag 6 for holding the medium 5 in close contact with the applicator; and an imaging probe 3 used for observing an affected part with ultrasonic waves.

Here, the medium 5 usually uses water as a material whose acoustic impedance is close to that of a living body so that the consistency between the living body and an ultrasonic transducer is satisfactorily maintained. Accordingly, the medium 5 is deaerated so as to prevent bubbles from being generated in the water as a result of high intensity ultrasonic wave exposure because the bubbles interfere with the transmission of the ultrasonic wave. In addition, an applicator handle 4 is attached to the rear end of the applicator 1. The applicator handle 4 is formed in such a shape that an operator such as a doctor can hold the applicator handle 4 with hands. This enables the operator to give treatment with the applicator 1 being held with hands.

The therapeutic ultrasound transducer 2 is drivingly controlled by the ultrasonic array driving unit 22 to emit high intensity ultrasonic waves. The therapeutic ultrasound transducer 2 is constituted of a plurality of ultrasonic transducers such as piezoelectric elements. The amplitude and phase of high-frequency power applied to the elements of the transducer 2 are independently controlled on an element basis.

Upon operation of an input unit 25, a therapeutic ultrasound control unit 23 receives information about ultrasound exposure. On the basis of the information, the control unit 23 gives an ultrasonic array driving unit 22 an exposure code signal which specifies a focus position and a shape of sound pressure distribution in an exposure sound field corresponding to a selected frequency. As a result, the ultrasonic array driving unit 22 drives each element of the therapeutic ultrasound transducer 2 to emit a high intensity ultrasonic wave, and thereby to heat and coagulate a focused region so that blood vessels are constricted or become infarcted.

On the other hand, a transmitted pulse supplied from a transmitted-pulse generation circuit 15 is subjected to focus processing in a transmission delay circuit 14, and is then amplified by an amplifier 13. After that, the amplified pulse is supplied to the imaging probe 3 through a transmit/receive separator 16.

A receive signal of an ultrasonic wave received from the living body by the imaging probe 3 is introduced through the transmit/receive separator 16 into an amplifier 17 where the receive signal is amplified. Then, a phase of the receive signal is adjusted in a receiving beam forming circuit 18 so that the receive signal from an arbitrary region in the living body is emphasized. On the basis of the receive signal output from the receiving beam forming circuit 18, a signal processor 19 generates an ultrasound tomographic image, which is then stored in a memory 260 and is displayed on a display 24.

In addition, among receive signals of ultrasonic waves obtained from the imaging probe 3, a frequency-deviating signal that is reflected from the blood flow in the living body is processed in a signal processor 19, and is then subjected to frequency analysis in a blood flow velocity analyzing unit 21, and thus the blood flow velocity is calculated. The calculated blood flow velocity is stored in the memory 260, and is displayed on the display 24.

The therapeutic ultrasound control unit 23, the blood flow velocity analyzing unit 21, the transmitted-pulse generation circuit 15, the signal processor 19, and the like, are controlled by instructions from the control unit 20. The control unit 20 is formed of, for example, a computer. Moreover, the ultrasonic imaging conditions and therapy conditions of the affected part can be arbitrarily set by an operator putting an execution order into the control unit 20 from the input unit 25.

A description will be below given of a case where the ultrasonic treatment equipment configured as described above is used to cause blood vessels of a tumor or the like to become infarcted so as to treat the tumor.

The ultrasonic treatment equipment according to this embodiment has an imaging mode and a therapy mode. In the imaging mode, for example, an affected part in a living body is imaged to acquire a tomographic image of the affected part, which is used for treatment. In the therapy mode, the affected part is exposed to a therapeutic ultrasonic wave according to the tomographic image acquired in the imaging mode, thereby being treated.

First of all, for example, an operator such as a doctor observes an affected part in the imaging mode. For example, when a tumor in abdomen such as uterine fibroid is to be treated, the applicator 1 is placed on a body surface 7 of a patient, and the water bag 6 is brought into close contact with the body surface 7 of the patient by use of ultrasonic wave jelly or the like. Next, the operator manually moves the applicator 1 in close contact with the body surface 7 of the patient while a degree of close contact with the body surface 7 of the patient is kept unchanged. In this way, the operator observes an ultrasound tomographic image of a patient body by use of the imaging probe 3 built into the applicator 1 as one unit.

When the operator puts into the input unit 25 an execution order to start imaging, the control unit 20 outputs an instruction to the transmitted-pulse generation circuit 15 and the transmission delay circuit 14 in response to the execution order. This instruction causes the transmitted-pulse generation circuit 15 and the transmission delay circuit 14 to operate, and consequently an imaging ultrasonic beam is emitted from the imaging probe 3 to the affected part. This imaging ultrasonic beam is scanned in an array direction of the imaging probe 3. As a result, a region along a fan-shaped tomographic plane of the affected part is exposed to the imaging ultrasonic beam.

The imaging probe 3 receives, as a receive signal, a reflection echo of the imaging ultrasonic wave reflected from the region to which the imaging ultrasonic wave has been applied. The receive signal is subjected to phasing processing on an imaging ultrasonic-beam basis in the receiving beam forming circuit 18. Then, the signal processor (including a digital scan converter) 19 generates the two-dimensional ultrasonic wave image of the tomographic plane. The tomographic image is stored in the memory 260 and is displayed on the display 24.

In addition, a frequency-deviating receive signal which is reflected from the blood flow in the living body is processed by the signal processor 19, and is then subjected to frequency analysis in the blood flow velocity analyzing unit 21 for calculation of blood flow velocity. The blood flow velocity calculated is stored in the memory 260. The blood flow velocity is displayed in color on the display 24 according to a value of the blood flow velocity.

To be more specific, by reading out the imaging data and blood flow velocity data which are stored in the memory 260, it is possible to display on the display 24 a tomographic image of the affected part 9 with the blood flow being superimposed on the tomographic image. The blood flow is displayed in color according to the velocity thereof. The operator can observe the blood vessels 10 of the affected part 9 by viewing a displayed image, and can make a treatment plan.

Figure 2:
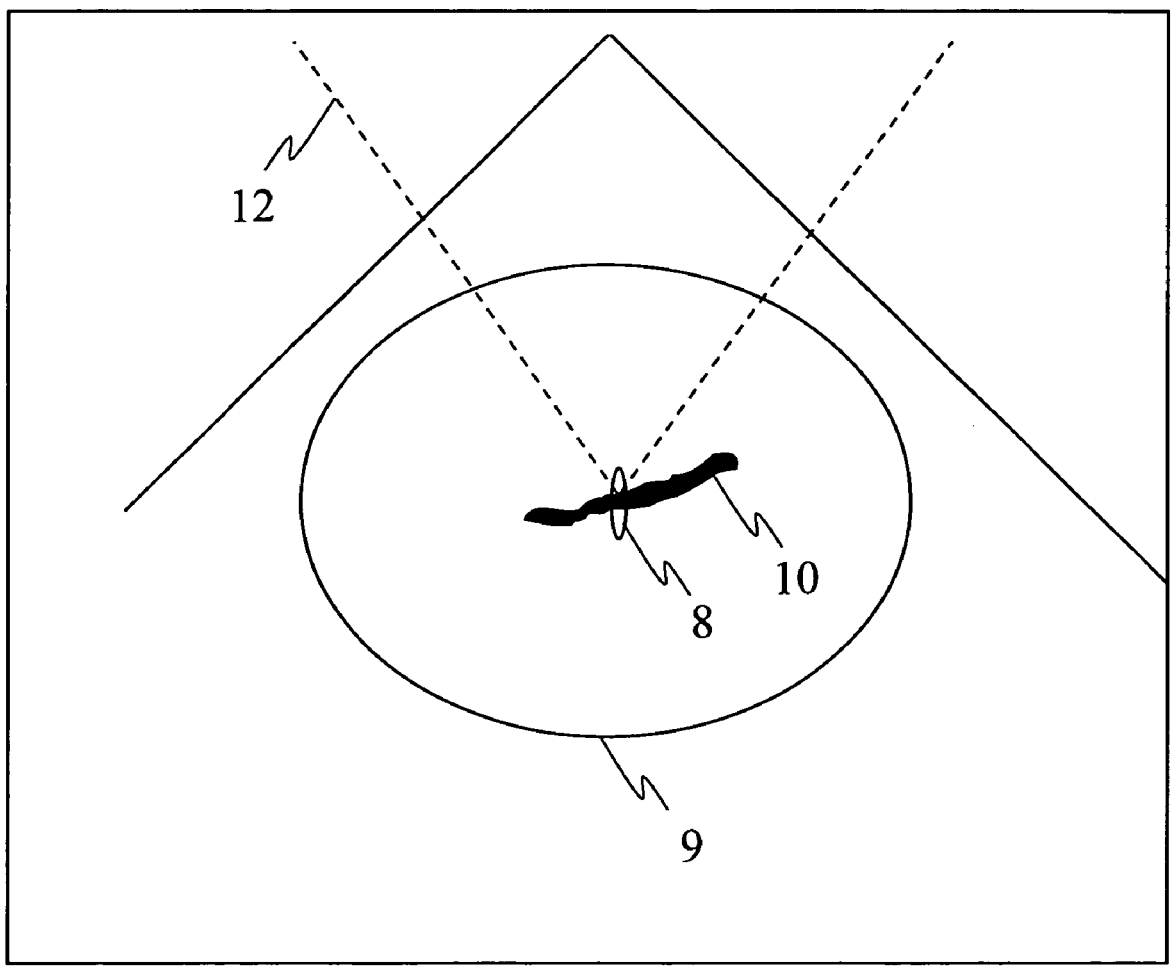
FIG. 2 is a schematic diagram illustrating an image that is displayed on a display before the therapeutic ultrasound exposure according to an embodiment of the present invention.

FIG. 2 is a schematic diagram illustrating an image that is displayed on a display before the therapeutic ultrasound exposure according to an embodiment of the present invention. FIG. 2 illustrates a tomographic image including the affected part 9 that is obtained by use of the imaging probe 3 included in the applicator. The operator can operate the input unit 25 while viewing the image displayed on the display 24. On this tomographic image, a focus 8 of the therapeutic ultrasonic wave is displayed beforehand. Accordingly, the operator can identify a position at which the therapeutic ultrasonic wave is aimed on the tomographic image that is currently being reviewed, and thus can easily aim the therapeutic ultrasonic wave at a blood vessel 10 to be treated.

Figure 3:
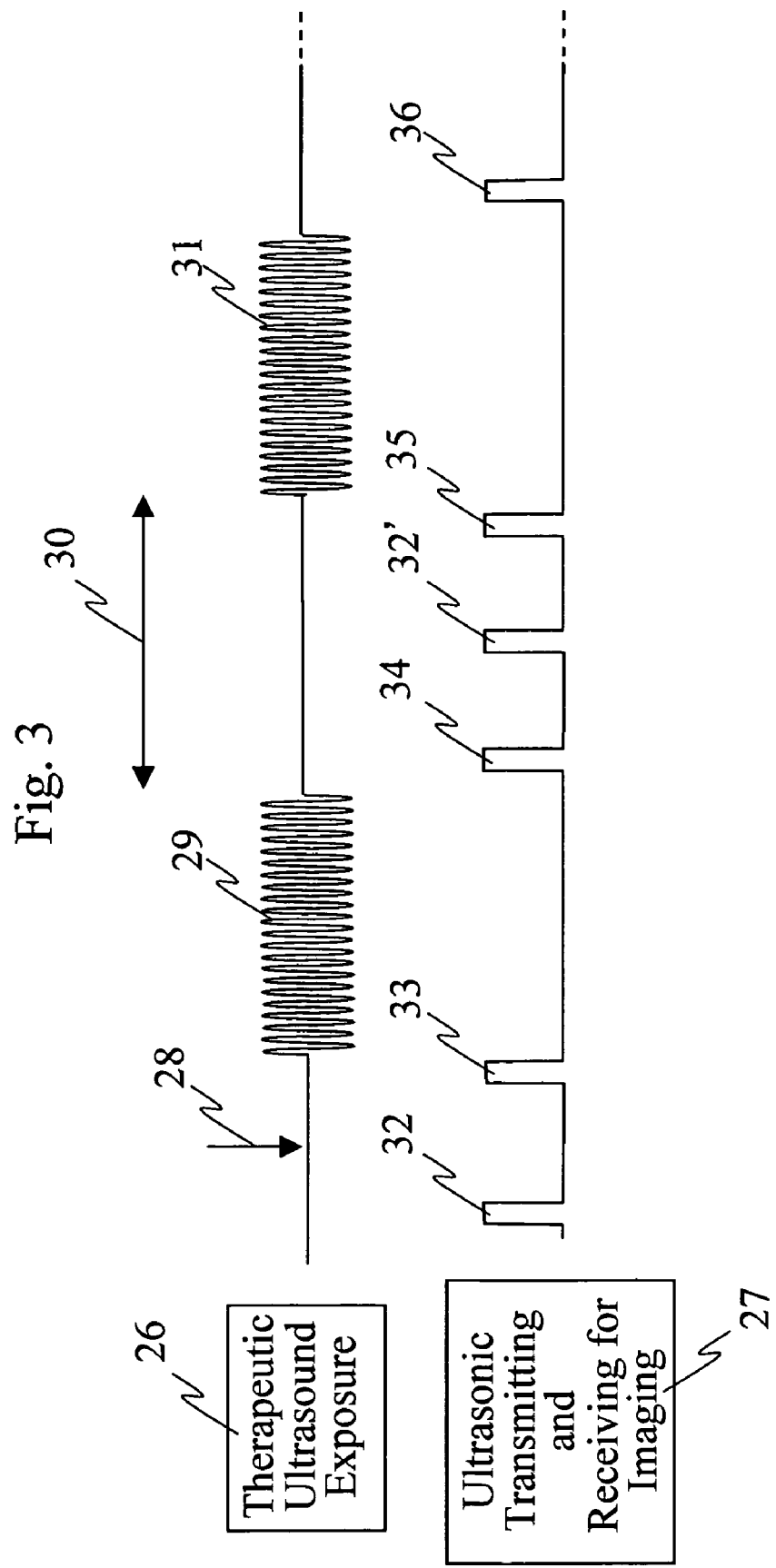
FIG. 3 is a schematic diagram illustrating the timing of ultrasonic transmitting and receiving for imaging, and the timing of therapeutic ultrasound exposure, according to an embodiment of the present invention.

FIG. 3 is a schematic diagram illustrating the timing of ultrasonic transmitting and receiving for imaging 27, and the timing of therapeutic ultrasound exposure 26, according to an embodiment of the present invention. In the embodiment shown in FIG. 3, a therapeutic ultrasonic wave which is a continuous wave is emitted a plurality of times.

The blood flow velocity of the blood vessel whose position is coincident with the focus 8 shown in FIG. 2 is measured by ultrasonic transmitting and receiving for imaging 32. To be more specific, a frequency-deviating receive signal which is reflected from the blood flow in the living body is processed by the signal processor 19, and is then subjected to frequency analysis in the blood flow velocity analyzing unit 21 for calculation of the blood flow velocity. The calculated blood flow velocity is stored in the memory 260. The blood flow velocity can also be displayed in color on the display 24 according to a value of the blood flow velocity.

Here, when the operator operates the input unit 25 to issue an execution order 28 for therapeutic ultrasound exposure, the control unit 20 controls ultrasonic transmitting and receiving for imaging 33 immediately before a first therapeutic ultrasound exposure 29. In response to a transmitted pulse, a frequency-deviating receive signal which is reflected from the blood flow in the living body is processed by the signal processor 19, and is then subjected to frequency analysis in the blood flow velocity analyzing unit 21 for calculation of the blood flow velocity. The calculated blood flow velocity is stored in the memory 260.

On completion of the ultrasonic transmitting and receiving for imaging 33, the first therapeutic ultrasound exposure 29 is performed. This first therapeutic ultrasound exposure 29 is performed with a continuous wave whose exposure time is about 1 through 30 sec. This exposure time is applied to heat coagulation therapy for usual tissue. Immediately after a predetermined exposure time lapsed and the first therapeutic ultrasound exposure 29 ended, ultrasonic transmitting and receiving for imaging 34 is controlled by the control unit 20. Thus, the blood flow velocity immediately after the first therapeutic ultrasound exposure is measured, and the measured blood flow velocity is then stored in the memory 260.

As described above, the blood flow velocity measured before the first therapeutic ultrasound exposure is compared with that measured after the first therapeutic ultrasound exposure, both of which are stored in the memory 260, so that a rate of change in blood flow velocity is calculated. If this rate of change in blood flow velocity exceeds a predetermined threshold value of a rate of change in blood flow velocity, an execution order signal for a second therapeutic ultrasound exposure is transmitted to the control unit 20. In another case, if the blood flow velocity immediately after the first therapeutic ultrasound exposure is within a range of an absolute value of the predetermined blood flow velocity, the following control is also possible. That is to say, an execution order signal for the second therapeutic ultrasound exposure is transmitted to the control unit 20, and at a point of time at which the blood flow velocity falls outside the range of the absolute value of the predetermined blood flow velocity, the exposure is stopped.

Upon receipt of the execution order signal for the second therapeutic ultrasound exposure, the control unit 20 controls the exposure timing of the imaging ultrasonic wave and that of the therapeutic ultrasonic wave. The control unit 20 can transmit a signal to the therapeutic ultrasound control unit 23 so that the exposure to the therapeutic ultrasonic wave can be performed according to a suspension period of therapy 30 between the first therapeutic ultrasound exposure and the second therapeutic ultrasound exposure, the exposure time of the second therapeutic ultrasonic wave, the intensity of exposure of the second therapeutic ultrasonic wave, and the like, which have been set beforehand at the time of initial setup.

After a lapse of the predetermined suspension period of therapy 30 of the therapeutic ultrasound exposure, the control unit 20 controls ultrasonic transmitting and receiving for imaging 35 immediately before the second therapeutic ultrasound exposure 31 is performed. Thus, the blood flow velocity is measured, and the measured blood flow velocity is then stored in the memory 260.

Subsequently, the second therapeutic ultrasound exposure 31 is performed, and immediately after the predetermined exposure time lapsed and the second therapeutic ultrasound exposure 31 ended, ultrasonic transmitting and receiving for imaging 36 is performed to measure the blood flow velocity, which is stored in the memory 260. As is the case with the first therapeutic ultrasound exposure, the blood flow velocity measured before the second therapeutic ultrasound exposure is compared with that after the second therapeutic ultrasound exposure, both of which are stored in the memory 260, so that a rate of change in blood flow velocity is calculated. If this rate of change in blood flow velocity exceeds the predetermined threshold value of the rate of change in blood flow velocity, an execution order signal for a third therapeutic ultrasound exposure is transmitted to the control unit 20. In this way, the timing of the therapeutic ultrasound exposure and the timing of ultrasonic transmitting and receiving for imaging are controlled.

Figure 4:
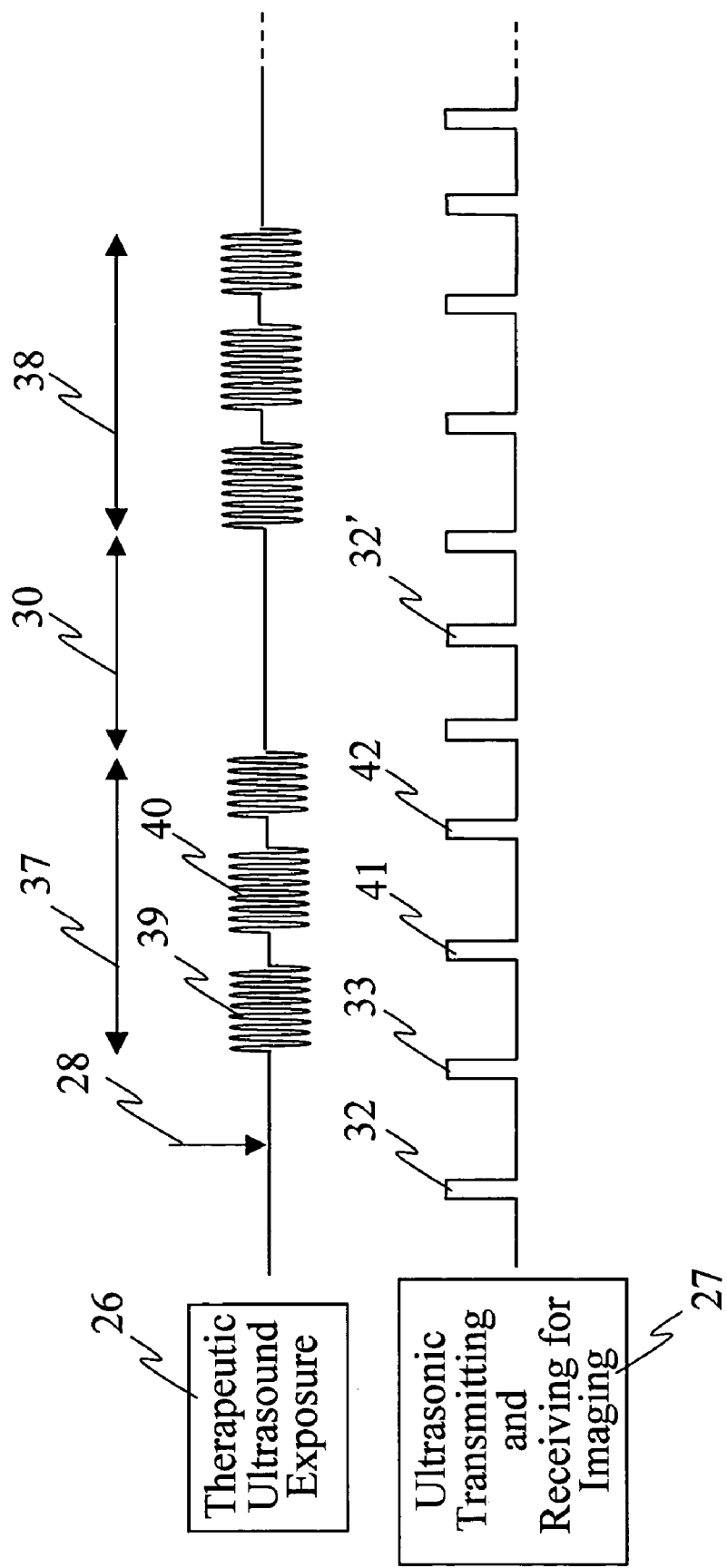
FIG. 4 is a schematic diagram illustrating the timing of ultrasonic transmitting and receiving for imaging, and the timing of therapeutic ultrasound exposure, according to an embodiment of the present invention.

FIG. 4 is a schematic diagram illustrating the timing of the ultrasonic transmitting and receiving for imaging 27 and the timing of the therapeutic ultrasound exposure 26 according to an embodiment of the present invention. FIG. 4 illustrates the timing of the therapeutic ultrasound exposure 26 and the timing of the ultrasonic transmitting and receiving for imaging 27 in a case where each therapeutic ultrasound exposure is not a continuous wave (as shown in FIG. 3) but a pulse wave. In the embodiment shown in FIG. 4, at each therapeutic ultrasound exposure, a therapeutic ultrasonic wave which is a pulse wave is emitted a plurality of times. The therapeutic ultrasound exposure is performed a plurality of times.

The blood flow velocity of the blood vessel whose position is coincident with the focus 8 shown in FIG. 2 is measured by ultrasonic transmitting and receiving for imaging 32. To be more specific, a frequency-deviating receive signal which is reflected from the blood flow in the living body is processed by the signal processor 19, and is then subjected to frequency analysis in the blood flow velocity analyzing unit 21 for calculation of the blood flow velocity. The calculated blood flow velocity is stored in the memory 260. The blood flow velocity can also be displayed in color on the display 24 according to a value of the blood flow velocity.

When the operator operates the input unit 25 to issue an execution order signal 28 for therapeutic ultrasound exposure, the control unit 20 controls ultrasonic transmitting and receiving for imaging 33 immediately before the first therapeutic ultrasound exposure 37. In response to a transmitted pulse, a frequency-deviating receive signal which is reflected from the blood flow in the living body is processed by the signal processor 19, and is then subjected to frequency analysis in the blood flow velocity analyzing unit 21 for calculation of the blood flow velocity. The calculated blood flow velocity is then stored in the memory 260.

Subsequently, the first therapeutic ultrasound exposure 37 is performed. However, this first therapeutic ultrasound exposure 37 is constituted of on-parts and off-parts included in a plurality of therapeutic ultrasonic waves. To be more specific, the therapeutic ultrasound control unit 23 is controlled on the basis of the amplitude of the ultrasonic wave, the pulse length, and a repeated period of the pulse wave, which have been predetermined. This makes it possible to emit a pulse-shaped therapeutic ultrasonic wave.

For example, the first therapeutic ultrasound exposure 37 is set at 60 sec, and the pulse length is set at 90 msec with a repeated period being kept at 9/10 for the period of 60 sec. In this setting, the therapeutic ultrasound exposure for the period of 90 msec is repeated at intervals of 10 msec which is an exposure suspension period.

After the first therapeutic ultrasound exposure 37 is started, ultrasonic transmitting and receiving for imaging 41 is performed during an exposure suspension period between the exposures of a first pulse wave 39 and a second pulse wave 40 included in the first therapeutic ultrasound exposure 37 to measure the blood flow velocity after the first pulse wave 39. The measured blood flow velocity is stored in the memory 260.

Also after the exposure of the second pulse wave 40, the blood flow velocity is measured by ultrasonic transmitting and receiving for imaging 42 in like manner. The measured blood flow velocity is then stored in the memory 260. In this way, the blood flow velocity after each exposure of the plurality of pulse waves included in the first therapeutic ultrasound exposure 37 is measured. The measured blood flow velocities after the corresponding exposures are stored in the memory 260.

Here, it becomes possible to compare the blood flow velocity immediately after the exposure to each pulse wave with the blood flow velocity immediately before the first therapeutic ultrasound exposure 37. For example, the following control becomes possible: if the blood flow velocity is within a range of an absolute value of the predetermined blood flow velocity, the exposure is continued. On the other hand, at a point of time at which the blood flow velocity falls outside the range of the absolute value of the predetermined blood flow velocity, the exposure is stopped.

Alternatively, if a change in blood flow velocity is within a range of a predetermined rate of change in blood flow velocity, the exposure is continued, and at a point of time at which the change in blood flow velocity falls outside the range of the predetermined rate of change in blood flow velocity, the exposure is stopped.

In FIGS. 3 and 4 described above, ultrasonic transmitting and receiving for imaging 32' is performed even during the suspension period of therapy 30 for calculation of the blood flow velocity. The calculated blood flow velocity is stored in the memory 260. The blood flow velocity can also be displayed in color on the display 24 according to a value of the blood flow velocity. This enables the operator to keep track of the blood flow velocity in a target region during the suspension period of therapy. To be more specific, even if the blood flow velocity unexpectedly varies during the suspension period of therapy, the operator can acquire information about the change, and thus can select the modification or temporary stop of a treatment plan.

Next, an example of a procedure for treating tumors with vessel infarction using ultrasonic treatment equipment according to this embodiment will be described below.

Figure 5:
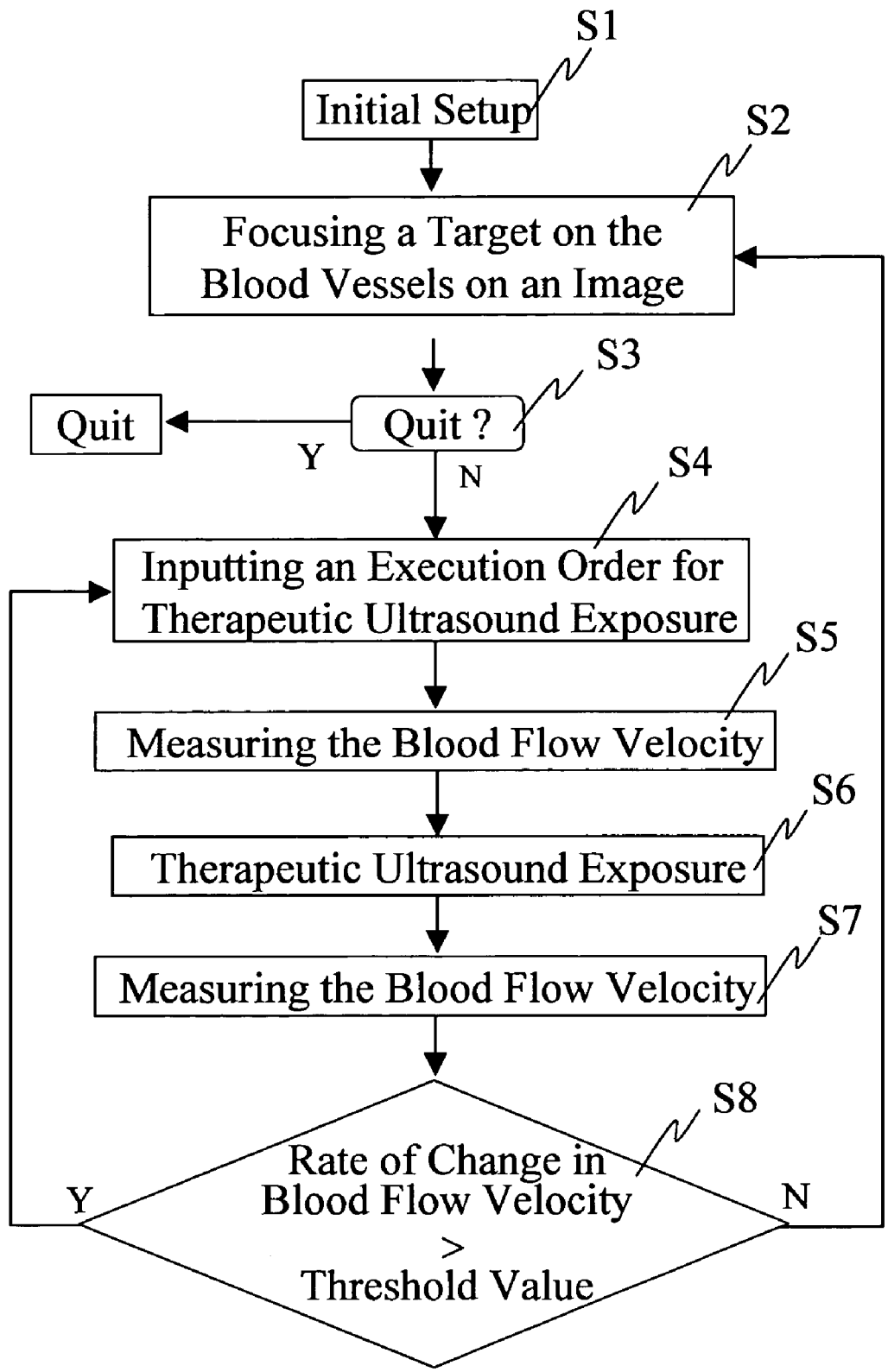
FIG. 5 is a flowchart illustrating treatment steps that use the ultrasonic treatment equipment according to the embodiment of the present invention.

FIG. 5 is a flowchart illustrating a treatment procedure that uses ultrasonic treatment equipment according to an embodiment of the present invention. Incidentally, symbol Si shown in FIGS. 5 and 6 means step i.

Symbol S1 is a step of performing an initial setup. An operator starts a therapy mode to perform the initial setup with a diagnostic image being displayed in real time on the display 25 in the above-mentioned imaging mode. In the initial setup, conditions are set so that the conditions may be suited to a target disease to be treated. For example, if an object is to cause feeding vessels of uterine fibroid to become infarcted, the intensity of a focused ultrasonic wave, a length of time required for each exposure, and the like, can be set. All of them are optimized beforehand with the object of achieving the vessel infarction of the uterine fibroid.

Subsequently, the operator observes an affected part 9 of a displayed imaging ultrasonic wave image, and further observes a target blood vessel 10 to be treated. To be more specific, while viewing the displayed image, the operator can select the target blood vessel 10 whose blood flow is to be interrupted by exposing the target blood vessel 10 to the focused ultrasonic wave.

Symbol S2 is a step of focusing a target on the blood vessels on an image. The operator holds the applicator 1, for example, by hand, and moves the applicator 1 so that the focus 8 may be properly placed on the target blood vessels 10 to be treated. At this time, by an execution order issued as a result of the operator's operation of the input unit 25, it is possible to measure the blood flow velocity of the blood vessel on which the focus 8 is placed. Moreover, the measured blood flow velocity of the blood vessel on which the focus 8 is placed can also be displayed on the display 24 with time.

Symbol S3 is a step by which the operator judges whether or not the blood vessel is to be exposed to a therapeutic ultrasonic wave. More specifically, the operator judges whether or not the blood vessel on which the focus 8 is placed is to be exposed to the therapeutic ultrasonic wave. If the operator judges that the blood vessel is to be exposed to the therapeutic ultrasonic wave, the process proceeds to S4 (a step of inputting an execution order for therapeutic ultrasound exposure). Here, the operator can input the execution order for therapeutic ultrasound exposure by operating the input unit 25.

Symbol S5 is a step of measuring the blood flow velocity of the blood vessel. When the execution order for therapeutic ultrasound exposure in S4 is triggered, the blood flow velocity of the blood vessel on which the focus 8 is placed is calculated in the blood flow velocity analyzing unit 21. The calculated blood flow velocity is then stored in the memory 260.

Symbol S6 is a step of performing the therapeutic ultrasound exposure. A first therapeutic ultrasound exposure is performed. Ultrasound exposure (condition) information set in S1 is inputted into the therapeutic ultrasound control unit 23. On the basis of the information, an exposure code signal which specifies a focus position and a shape of sound pressure distribution in an exposure sound field corresponding to a selected frequency is given to the ultrasonic array driving unit 22. As a result, the ultrasonic array driving unit 22 drives each element of the therapeutic ultrasound transducer 2, whereby a strong ultrasonic wave is emitted according to the predetermined exposure time.

Symbol S7 is a step of measuring the blood flow velocity of the blood vessel. The blood flow velocity of the blood vessel after the exposure to the ultrasonic wave at a part on which the focus 8 is placed is calculated in the blood flow velocity analyzing unit 21. The blood flow velocity is then stored in the memory 260.

Symbol S8 is a step of comparing a rate of change in blood flow velocity with a threshold value thereof. The blood flow velocity analyzing unit 21 compares the blood flow velocity before the therapeutic ultrasound exposure (the blood flow velocity acquired in S5) with the blood flow velocity after the therapeutic ultrasound exposure (the blood flow velocity acquired in S7), both of which are stored in the memory 260. Next, the blood flow velocity analyzing unit 21 calculates the rate of change in blood flow velocity, which is then stored in the memory 260. To be more specific, a rate of change in blood flow velocity $R1$ is calculated from the blood flow velocity $V1$ and the blood flow velocity $V2$ both at the focus 8, using equation (1), and is then stored in the memory 260. The blood flow velocity $V1$ has been measured before the therapeutic ultrasound exposure, whereas the blood flow velocity $V2$ has been measured immediately after the exposure.

$$R1 = V2/V1 \tag{1}$$

Here, if the calculated rate of change in blood flow velocity exceeds the predetermined threshold value, the therapeutic ultrasound exposure causes the blood vessel to be constricted. As a result, it is judged that the blood flow velocity has increased. Accordingly, the process returns from S8 to S4 where an execution order for second exposure of the same region to therapeutic ultrasound is generated again. To be more specific, steps from S4 to S7 are repeated again in like manner.

The second therapeutic ultrasound exposure of the same region is performed. Then, as is the case with the first exposure, the blood flow velocity before the exposure is compared with that after the exposure. If the rate of change in blood flow velocity exceeds the predetermined threshold value in S7, the second therapeutic ultrasound exposure causes the blood vessels to be constricted. Accordingly, it is judged that the blood flow velocity has increased.

The process returns from S8 to S4 again, and then a third therapeutic ultrasound exposure is performed. Thus, it is possible to calculate a degree of vessel constriction on a therapeutic ultrasound exposure basis. In addition, repeatedly exposing the same region to an ultrasonic wave makes it possible to cause the vessel constriction to progress. As a result, the blood flow of the targeted blood vessel is eventually stopped, which causes vessel infarction.

On the other hand, the rate of change in blood flow velocity before and after the therapeutic ultrasound exposure may be lower than or equal to the predetermined threshold value in S8. This means that the therapy ultrasound exposure results in insufficient constriction of the blood vessel, or that no blood flow could be detected. Accordingly, the process returns from S8 to S4.

The operator can observe the blood vessel again, and can also focus a target on the blood vessel again. Here, in S3, the operator can choose to treat the blood vessel 10 on which the focus 8 is placed again, or to end the treatment. For example, if the blood flow is completely stopped, or the measurement of the blood flow is unstable, the operator can end the treatment. On the other hand, if the operator chooses to perform the exposure again, the process proceeds to S4, where it is possible to continue the treatment again according to the above steps.

In addition, by displaying the blood flow velocity calculated and stored in the memory 260 in S5 and S7 on the display 24 with time, the operator can at any time keep track of a change in blood flow of the blood vessel being treated. In another case, the operator can also display with time the rate of change in blood flow velocity calculated in S8 on the display 24.

Figure 6:
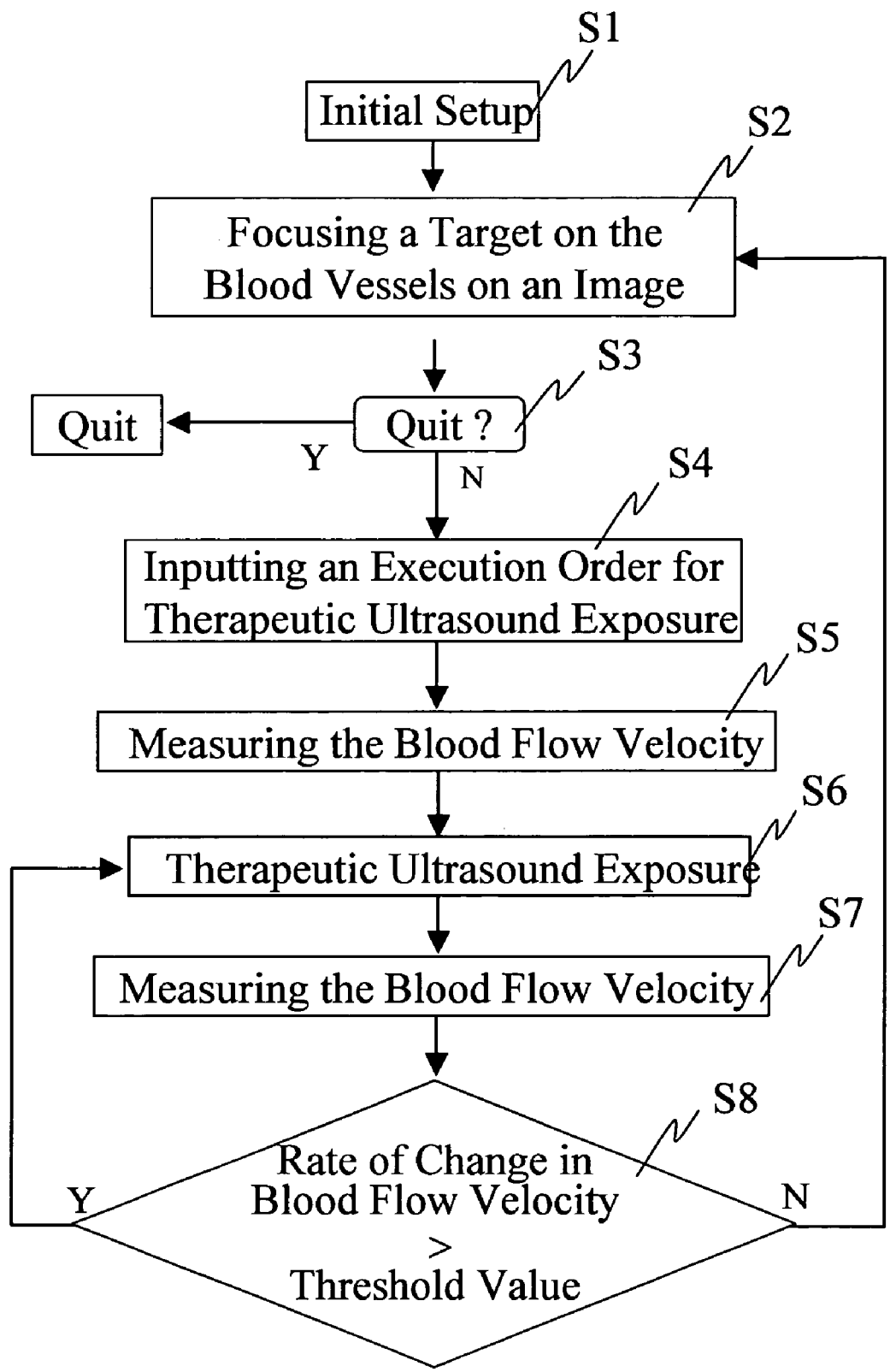
FIG. 6 is a flowchart illustrating another series of treatment steps that use the ultrasonic treatment equipment according to an embodiment of the present invention.

FIG. 6 is a flowchart illustrating another series of treatment steps that use the ultrasonic treatment equipment according to the embodiment of the present invention. By predetermining conditions of therapeutic ultrasound exposure in S1 of FIG. 5, the treatment steps as shown in the flowchart of FIG. 6 become possible. To be more specific, it can also be so configured that if a rate of change in blood flow velocity is larger than or equal to the predetermined threshold value in S8, the process directly proceeds to the therapeutic ultrasound exposure in S6 so as to quickly perform the therapeutic ultrasound exposure.

Figure 7:
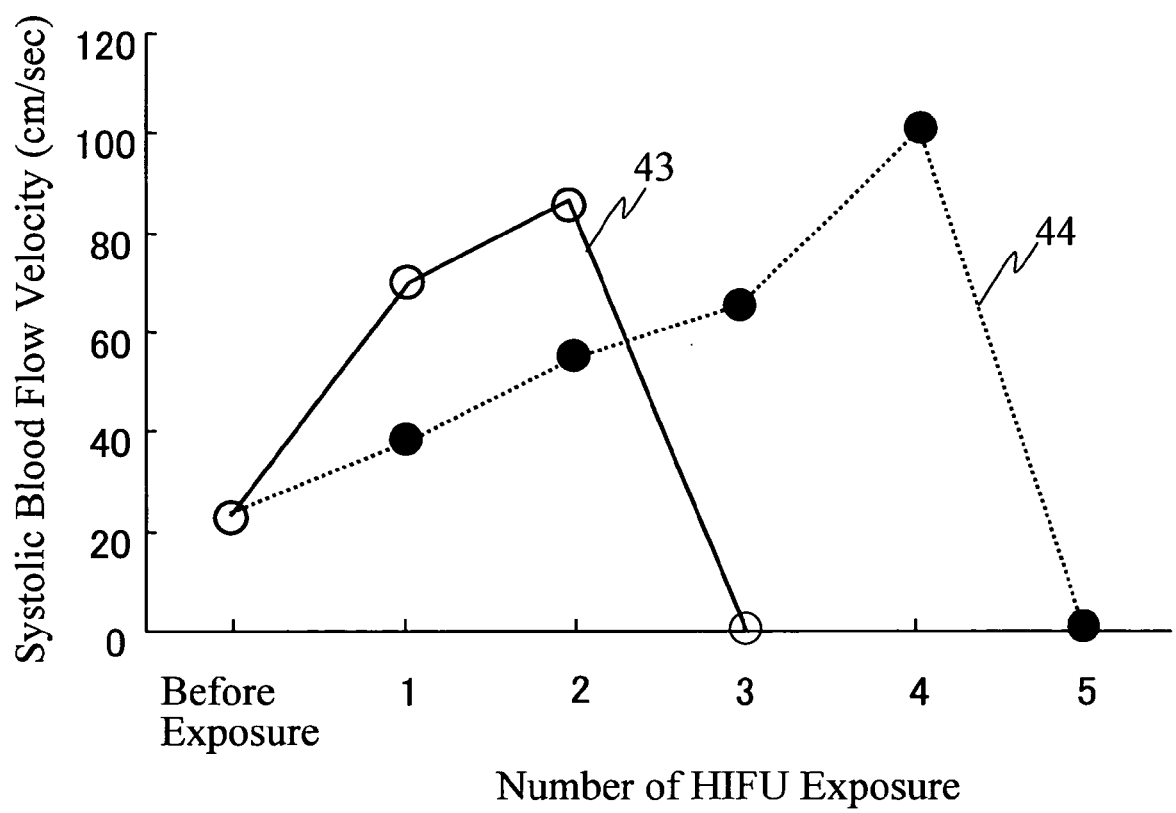
FIG. 7 is a graph illustrating the result of measuring the blood flow velocity of a femoral artery of a rat before and after the focused ultrasound exposure according to the embodiment of the present invention.

FIG. 7 is a graph illustrating the results of measuring the blood flow velocity of a femoral artery of a rat before and after the focused ultrasound exposure according to the embodiment of the present invention. A horizontal axis in FIG. 7 indicates the number of times HIFU (High Intensity Focused Ultrasound) exposure is performed. A vertical axis in FIG. 7 indicates the systolic blood flow velocity (cm/sec). FIG. 7 shows changes in blood flow velocity in a case where the femoral artery of the rat is exposed to a focused ultrasonic wave having a frequency of 3 MHz a plurality of times. Two examples whose measurement results are shown with white circles 43 and black circles 44 respectively in FIG. 7 will be described below.

A threshold value of a rate of change in blood flow velocity is set beforehand. For example, for each change in blood flow velocity of the blood vessel of the rat shown in FIG. 7, if the blood flow velocity is, for example, 1.2 times as high as the blood flow velocity before the exposure or more (in other words, a rate of change in blood flow velocity is 1.2 or more), the exposure is repeated. On the other hand, if the blood flow velocity does not exceed 1.2 times as high as the blood flow velocity before the exposure, the exposure is temporarily stopped and a focus is placed again. The systolic blood flow velocity is measured as the blood flow velocity. In the example of the rat indicated with the white circles 43 in FIG. 7, the blood flow velocity before the focused ultrasound exposure is about 20 cm/sec. As a result of the first exposure, the blood flow velocity increases to about 70 cm/sec. Since the rate of change in blood flow velocity is higher than 1.2, which is the predetermined threshold value, the second exposure is performed. Since the blood flow velocity after the second exposure is about 82 cm/sec, a rate of change in blood flow velocity before and after the second exposure exceeds 1.2, which is the predetermined threshold value. Accordingly, the third exposure is performed. Since the third exposure causes the blood flow to be interrupted, the result of measuring the blood flow velocity is 0 cm/sec. Accordingly, a rate of change in blood flow velocity before and after the third exposure becomes lower than the set value, and consequently the exposure is stopped.

Likewise, an example of the rat indicated with the black circles 44 will be described. As a result of the first exposure, the blood flow velocity increases from 20 cm/sec to about 40 cm/sec. Accordingly, a rate of change in blood flow velocity is higher than the predetermined threshold value, and consequently the second exposure is performed. Since a change in blood flow velocity before and after the second exposure is also larger than the set value, the third exposure is performed in like manner. The exposure is repeated up to the fifth exposure in like manner thereafter. Since the fifth exposure eventually interrupts the blood flow, the blood flow velocity becomes 0 cm/sec, and accordingly a rate of change in blood flow velocity becomes lower than the predetermined threshold value. As a result, the exposure is stopped at this point of time.

In this way, by comparing a rate of change in blood flow velocity with the threshold value for each exposure, it is possible to judge a degree of constriction of the blood vessel or a degree of infarction of the blood vessel on an exposure basis, and thereby to change on a target blood vessel basis the number of times the exposure is performed. This makes it possible to interrupt the blood vessel with certainty.

Figure 8:
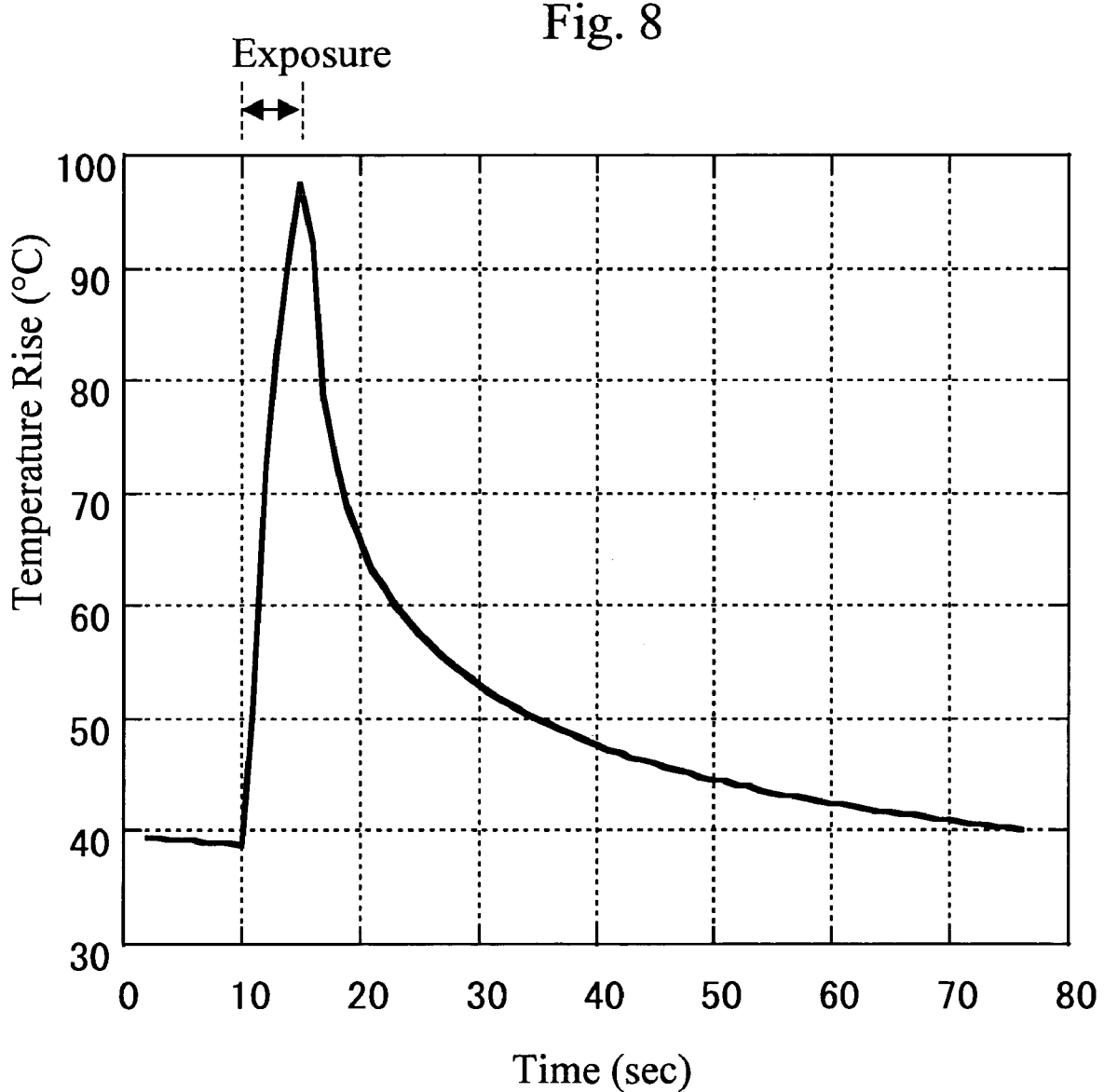
FIG. 8 is a graph illustrating a change in temperature of a femoral artery of a rat, which is caused by the focused ultrasound exposure according to the embodiment of the present invention.

FIG. 8 is a graph illustrating a change in temperature of a femoral artery of a rat, which is caused by the focused ultrasound exposure according to the embodiment of the present invention. A horizontal axis in FIG. 8 indicates time (sec); and a vertical axis in FIG. 8 indicates a change in temperature (° C.). FIG. 8 shows the results of measuring an increase in temperature inside a focused tissue by inserting a thermocouple into an affected part when the blood vessel of the above-mentioned rat is exposed to a focused ultrasonic wave.

A length of time during which the focused ultrasound exposure is performed is 5 sec. FIG. 8 shows that the ultrasound exposure causes the temperature inside the tissue to rapidly increase. More specifically, it is found that the ultrasound exposure for 5 sec causes the temperature inside the tissue to increase to about 100° C. It is highly probable that the blood vessel can be constricted or become infarcted by exposing the blood vessel and the tissue surrounding the blood vessel to a focused ultrasonic wave to cause heat denaturation thereof.

Figure 9:
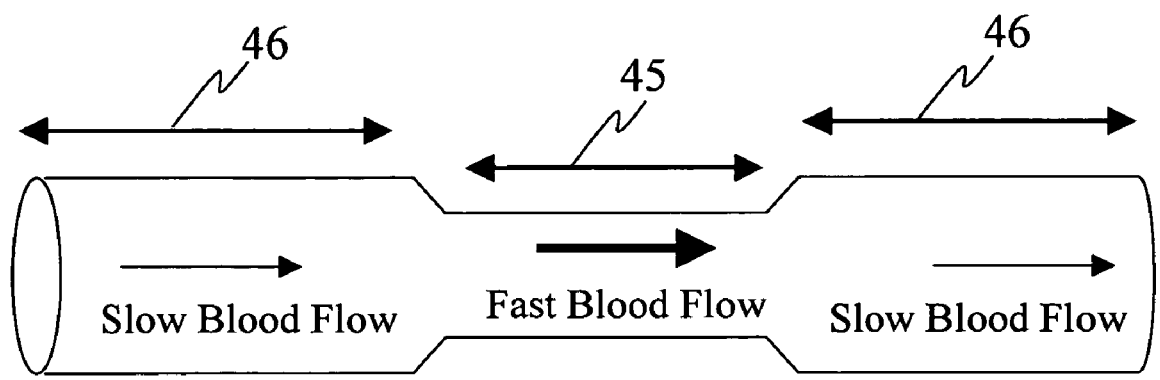
FIG. 9 is a schematic diagram illustrating a blood vessel.

FIG. 9 is a schematic diagram illustrating a blood vessel. In an example shown in FIG. 9, the blood vessel includes vessel constriction. By aiming a focused ultrasonic wave at the blood vessel to perform exposure, denaturation occurs in the blood vessel tissue or the tissue surrounding the blood vessel, causing the blood vessel to be constricted. The blood flow velocity in a region of vessel constriction 45 becomes faster than that of a normal blood vessel region 46. According to the present invention, detecting a change in blood flow velocity in the region of vessel constriction as shown in FIG. 9 makes it possible to keep track of a degree of vessel constriction, or a degree of infarction, caused by the focused ultrasound exposure.

The reference numerals used in the drawings will be described below.

1 . . . Therapeutic applicator, 2 . . . Therapeutic ultrasound transducer, 3 . . . Imaging probe, 4 . . . Applicator handle, 5 . . . Medium, 6 . . . Water bag, 7 . . . Skin, 8 . . . Focus, 9 . . . Affected part, 10 . . . Blood vessel, 11 . . . Patient, 12 . . . Therapeutic ultrasonic beam, 13 . . . Amplifier, 14 . . .

Transmission delay circuit, 15 . . . Transmitted-pulse generation circuit, 16 . . . Transmit/receive separator, 17 . . . Amplifier, 18 . . . Receiving beam forming circuit, 19 . . . Signal processor, 20 . . . Control unit, 21 . . . Blood flow velocity analyzing unit, 22 . . . Ultrasonic array driving unit, 23 . . . Therapeutic ultrasound control unit, 24 . . . Display, 25 . . . Input unit, 260 . . . Memory, 26 . . . Therapeutic ultrasound exposure, 27 . . . Ultrasonic transmitting and receiving for imaging, 28 . . . Execution order for therapeutic ultrasound exposure, 29 . . . First therapeutic ultrasound exposure, 30 . . . Suspension period of therapy, 31 . . . Second therapeutic ultrasound exposure, 32, 32', 33, 34, 35, 36 . . . Ultrasonic transmitting and receiving for imaging, 37 . . . First therapeutic ultrasound exposure, 38 . . . Second therapeutic ultrasound exposure, 39 . . . First pulse wave, 40 . . . Second pulse wave, 41, 42 . . . Ultrasonic transmitting and receiving for imaging, 43 . . . One example of a rat with blood flow measurement, 44 . . . One example of a rat with blood flow measurement, 45 . . . Region of vessel constriction, 46 . . . Region of normal blood vessel.

According to the present invention, it is possible to cause a target blood vessel to certainly become infarcted by repeating exposure while measuring a degree of vessel constriction on a therapeutic ultrasound exposure basis.

What is claimed is:

1. An ultrasonic treatment equipment comprising:
   a therapeutic ultrasonic transducer which exposes a blood vessel of an affected part to a focused therapeutic ultrasonic wave for a specified period of exposure time;
   an imaging ultrasonic probe which images an ultrasound tomographic image of the affected part;
   a display unit which displays the ultrasound tomographic image;
   means for comparing a blood flow velocity of the blood vessel before the exposure to the therapeutic ultrasonic wave with that after the exposure to the therapeutic ultrasonic wave, and calculating a rate of change in blood flow velocity; and
   a control unit for controlling the exposure to the therapeutic ultrasonic wave based on the rate of change in blood flow velocity for causing the blood vessel of the affected part to be constricted or become infracted,
   wherein if the rate of change in blood flow velocity before and after the exposure to the therapeutic ultrasonic wave is within a range of a predetermined rate of change, the control unit repeats the exposure to the therapeutic ultrasonic wave, whereas if the rate of change in blood flow velocity before and after the exposure to the therapeutic ultrasonic wave is out of the range of the predetermined rate of change, the control unit ends the exposure to the therapeutic ultrasonic wave.

2. The ultrasonic treatment equipment according to claim 1, further comprising:
   means for detecting a blood flow signal from a signal received by the imaging ultrasonic probe and determining the blood flow velocity of the blood vessel of the affected part.

3. The ultrasonic treatment equipment according to claim 1, wherein:
   said blood flow velocity before and after the exposure to the therapeutic ultrasonic wave and a rate of change in blood flow velocity before and after the exposure, are displayed on the display unit together with the ultrasound tomographic image of the affected part.

4. The ultrasonic treatment equipment according to claim 1, wherein:
   a vessel constriction rate acquired on the basis of the rate of change in blood flow velocity before and after the exposure to the therapeutic ultrasonic wave is displayed on the display unit together with the ultrasound tomographic image of the affected part.

5. The ultrasonic treatment equipment according to claim 1, wherein:
   at least one of: the number of times the exposure is repeated, the intensity of the exposure, and the specified exposure time, is displayed on the display unit together with the ultrasound tomographic image of the affected part.

6. The ultrasonic treatment equipment according to claim 1, wherein:
   a region that is exposed to the therapeutic ultrasonic wave and exposure conditions of the therapeutic ultrasonic wave, are displayed on the display unit together with the ultrasound tomographic image of the affected part.

7. The ultrasonic treatment equipment according to claim 1, wherein:
   said ultrasound tomographic image of the affected part is displayed in time series on the display units together with exposure conditions of the therapeutic ultrasonic wave to which the affected part has been exposed a plurality of times.

8. An ultrasonic treatment equipment comprising:
   a therapeutic ultrasonic transducer which exposes a blood vessel of an affected part to a focused therapeutic ultrasonic wave for a specified period of exposure time;
   an imaging ultrasonic probe which images an ultrasound tomographic image of the affected part;
   a display unit which displays the ultrasound tomographic image;
   means for detecting a blood flow signal from a signal received by the imaging ultrasonic probe and determining the blood flow velocity of the blood vessel of the affected part; and
   a control unit for controlling the exposure to the therapeutic ultrasonic wave on the basis of a change in the blood flow velocity before and after the exposure to the therapeutic ultrasonic wave,
   wherein if the change in blood flow velocity is an increasing change, the control unit repeats the exposure to the therapeutic ultrasonic wave.

9. The ultrasonic treatment equipment according to claim 8, wherein:
   the exposure to the therapeutic ultrasonic wave causes the blood vessel of the affected part to be constricted or become infarcted.

10. The ultrasonic treatment equipment according to claim 9, wherein:
    a region that is exposed to the therapeutic ultrasonic wave and exposure conditions of the therapeutic ultrasonic wave, are displayed on the display unit together with the ultrasound tomographic image of the affected part.

11. The ultrasonic treatment equipment according to claim 9, wherein:
    said ultrasound tomographic image of the affected part is displayed in time series on the display unit, together with exposure conditions of the therapeutic ultrasonic wave to which the affected part has been exposed a plurality of times.

12. The ultrasonic treatment equipment according to claim 8, wherein:

if the change in blood flow velocity is a decreasing change, and the blood flow velocity after the exposure to the therapeutic ultrasonic wave is lower than or equal to a predetermined threshold value, the control unit ends the exposure to the therapeutic ultrasonic wave.

13. The ultrasonic treatment equipment according to claim 8, wherein:

the blood flow velocity before and after the exposure to the therapeutic ultrasonic wave and a rate of change in the blood flow velocity before and after the exposure, are displayed on the display unit together with the ultrasound tomographic image of the affected part.

14. The ultrasonic treatment equipment according to claim 8, wherein:

a vessel constriction rate acquired on the basis of the rate of change in blood flow velocity before and after the exposure to the therapeutic ultrasonic wave, is displayed on the display unit together with the ultrasound tomographic image of the affected part.

* * * * *